(12) United States Patent
Lackner

(10) Patent No.: US 9,131,921 B2
(45) Date of Patent: Sep. 15, 2015

(54) COVER FOR AN ULTRASONIC HEAD

(76) Inventor: Leopold Lackner, Ybbs (AT)

( * ) Notice: Subject to any disclaimer, the term of this patent is extended or adjusted under 35 U.S.C. 154(b) by 0 days.

(21) Appl. No.: 13/988,290

(22) PCT Filed: Nov. 4, 2011

(86) PCT No.: PCT/EP2011/069413
§ 371 (c)(1),
(2), (4) Date: Jun. 14, 2013

(87) PCT Pub. No.: WO2012/065859
PCT Pub. Date: May 24, 2012

(65) Prior Publication Data
US 2014/0042045 A1 Feb. 13, 2014

(30) Foreign Application Priority Data
Nov. 19, 2010 (AT) ................. GM707/2010

(51) Int. Cl.
*B65D 85/38* (2006.01)
*A61B 8/00* (2006.01)
*A61B 19/08* (2006.01)

(52) U.S. Cl.
CPC ............. *A61B 8/44* (2013.01); *A61B 19/081* (2013.01); *A61B 2019/083* (2013.01)

(58) Field of Classification Search
CPC .................................. A61B 8/44; B65D 85/38
USPC .................... 350/61, 65, 67; 206/305
See application file for complete search history.

(56) References Cited

U.S. PATENT DOCUMENTS

| 3,528,720 | A | * | 9/1970 | Treace | 359/510 |
| 3,698,791 | A | * | 10/1972 | Walchle et al. | 359/510 |
| 3,796,477 | A | * | 3/1974 | Geraci | 359/511 |
| 5,311,358 | A | * | 5/1994 | Pederson et al. | 359/510 |
| 5,467,223 | A | * | 11/1995 | Cleveland et al. | 359/510 |
| 6,116,741 | A | * | 9/2000 | Paschal | 359/510 |
| 2006/0264751 | A1 | * | 11/2006 | Wendelken et al. | 600/439 |

FOREIGN PATENT DOCUMENTS

| DE | 20 2007 003259 U1 | 11/2007 |
| DE | 10 2007 007742 A1 | 8/2008 |
| WO | WO 2007/011689 A2 | 1/2007 |

OTHER PUBLICATIONS

Lackner, Leopold, PCT/EP2011/069413, International Search Report mailed Jan. 3, 2012, 3 pages.

* cited by examiner

*Primary Examiner* — Anthony Stashick
*Assistant Examiner* — Jennifer N Zettl
(74) *Attorney, Agent, or Firm* — McKee, Voorhees & Sease, PLC

(57) ABSTRACT

A film tube which is arranged in the manner of a bag for enclosing a hand-operated ultrasonic transducer (8) and the cable leads thereof, and in which an adhesive surface (3) is provided for attaching the film tube to the ultrasonic transducer (8). It is proposed in accordance with the invention that a support (9) for the adhesive surface (3) is provided and the film tube comprises a sound opening (10) in the region of the adhesive surface (3), with the support (9) covering the sound surface (10) and being tightly connected with the film tube. A film tube is therefore provided by means of the invention which protects the ultrasonic transducer (8), and especially its sound surface, in the best possible way and avoids the use of a gel between the ultrasonic transducer (8) and the film tube. Even frequent attachment and removal of the adhesive surface (3) does not impair the sound surface because the adhesive surface (3) can be detached from the ultrasonic transducer (8) without any residues.

7 Claims, 2 Drawing Sheets

COVER FOR AN ULTRASONIC HEAD

CROSS-REFERENCE TO RELATED APPLICATIONS

This is a National Phase application claiming priority to PCT/EP2011/069413 filed Nov. 4, 2011, which claims priority to GM 707/2010 filed Nov. 19, 2010, all of which are herein incorporated by reference in their entireties.

The invention relates to a film tube which is arranged in the manner of a bag for enclosing a hand-operated ultrasonic transducer and the cable leads thereof, and in which an adhesive surface is provided for attaching the film tube to the ultrasonic transducer, according to the preamble of claim 1.

Hand-operated ultrasonic transducer devices are used in medicine for supporting medical diagnostics and the treatment of patients, wherein the sound surface of the ultrasonic transducer (i.e. the outlet surface of the ultrasonic sound on the ultrasonic transducer) is guided with slight pressure on the body of the patient. The ultrasonic waves are generated by means of special crystals incorporated in the ultrasonic transducer via piezoelectric effect. In this process, a high-frequency electrical alternating voltage produces excitation to make the crystals oscillate, which cause pressure fluctuations in form of ultrasonic sound. Conversely, an ultrasonic wave impinging on the crystal generates a measurable electrical voltage which will be displayed by the ultrasonic device as a pixel. The ultrasonic transducer is usually made of hard plastic, but in the region of the outlet surface of the ultrasonic sound an elastic material such as caoutchouc is mostly provided.

The relevant aspect for meaningful imaging is good sound transmission from the sound surface to the body of the patient. For the purpose of improving sound transmission, a special gel is usually used which is applied to the body of patient. Ultrasonic sound will propagate very well in fluid or gel-like media, but very badly in gaseous media. Gaseous transmission media therefore represent optically denser areas which therefore lead to undesirable reflections and diffractions of the ultrasonic sound which impair imaging. The ultrasonic transducer is usually also enclosed by a film tube for reasons of hygiene, which film tube can also be arranged in a sterile manner. Since the mere wrapping of the sound surface with a film can also lead to air pockets as a result of the formation of folds which impair the quality of the ultrasonic image, a gel must also be applied between the ultrasonic transducer and the film tube, which is perceived however in daily application as laborious and unpleasant.

That is why it was also proposed to fasten the ultrasonic transducer to the film tube by means of an all-over adhesive surface. As a result, a fold-free transition between the film cover and the sound surface can be ensured without any air pockets, therefore not requiring any additional gel layer between the ultrasonic transducer and the inside of the film for sound transmission.

The problem arises in this respect however that as a result of frequent attachment and detachment of the adhesive surface from the ultrasonic transducer the sound surface may be damaged, e.g. the caoutchouc membrane or the oscillating piezoelectric crystals, which entails expensive repairs. Furthermore, residues of the adhesive will often remain on the ultrasonic transducer, which need to be removed with much effort and which may damage the ultrasonic transducer due to frequent cleaning.

That is why it was subsequently also proposed that the adhesive surface is arranged in an annular fashion and encloses an adhesive-free surface which in its expansion substantially corresponds to the outlet surface of the sound waves on the ultrasonic transducer in order to avoid residues of the adhesive on the sensitive areas of ultrasonic transducer. It was noticed in such an embodiment however that the film tube cannot be kept in its position in a sufficiently fold-free manner, so that the transition between the film cover and the sound surface cannot be ensured without any air pockets. Imaging therefore does not produce any satisfactory results.

It is therefore the object of the invention to provide a film tube which on the one hand avoids the use of gel as a transmission medium between the sound head and the film tube, but protects the sound head to a substantial extent on the other hand, even in the case of frequent use of a film tube cover. Furthermore, residues of the adhesive on the sound head shall be avoided to the highest possible extent. These objects are achieved by the features of claim 1.

Claim 1 relates to a film tube which is arranged in the manner of a bag for enclosing a hand-operated ultrasonic transducer and its cable leads, and in which an adhesive surface is provided for fixing the film tube to the ultrasonic transducer. It is provided in accordance with the invention that a support for the adhesive surface is provided and the film tube comprises a sound opening in the region of the adhesive surface, with the support covering the sound opening and being tightly connected with the film tube.

It would also be possible to provide a support for the adhesive surface which is provided on its side facing the ultrasonic transducer with a first adhesive of low adhesive force, which therefore remains completely on the support during detachment from the ultrasonic transducer, and with a second adhesive of comparatively high adhesive force on the side facing away from the ultrasonic transducer in order to fix the support securely to the film tube. In this case, the ultrasonic transducer would be separated from the body of the patient by a sequence of four layers, which are the overall adhesive layer of the first adhesive of low adhesive force, the support layer, the overall adhesive layer of the second adhesive of higher adhesive force, and the actual film tube. This sequence of four layers impairs imaging quality, even though residues of the first adhesive on the ultrasonic transducer can successfully be prevented in this manner.

That is why it is provided in accordance with the invention to provide the film tube with a sound opening, i.e. a recess in the film tube, in order to avoid a separating layer provided by the film tube in the passage region of the sound waves, and to use the support of the adhesive surface as a cover in this area, which for this purpose is tightly connected (usually impermeable to germs) with the film tube. As a result, two separating layers of the aforementioned four separating layers can be avoided, namely the layer provided by the film tube and the adhesive layer of the second adhesive. The measures in accordance with the invention allow realizing an adhesive surface of low adhesive force by using a suitable support on the one hand, which adhesive surface can be detached without any residues from the ultrasonic transducer, and allow achieving good imaging on the other hand by means of the sound opening. Furthermore, no additional medium such as a gel between the transducer and the inside of the film is required for sound transmission.

The tight connection between the support and the film tube can be realized in different ways, e.g. by welding. For this purpose, the support and the film tube are respectively made of a thermoplastic material in order to enable welding of the support with the film tube. A welded connection between two plastic materials usually represents a connection which is impermeable to germs.

It is alternatively proposed that the adhesive surface for fixing the film tube to the ultrasonic transducer is formed by a first adhesive, and the support is tightly connected with the film tube by means of a second adhesive. This embodiment allows an especially simple and cost-effective production of the film tube in accordance with the invention.

As will be described below in closer detail, there are principally two possibilities for fixing the support to the film tube, namely on the side of the film tube which faces the ultrasonic transducer in the in-use position, and on its side facing away. In accordance with a preferred embodiment, the first possibility is proposed, so that the first adhesive and the second adhesive are arranged on opposite sides of the support. Since the support covers the sound opening, the second adhesive will therefore be applied in an annular fashion to the support in order to produce a tight connection with the areas of the film tube enclosing the sound opening.

The use of a support for the adhesive surface and its arrangement in the region of the sound opening offers the considerable advantage that the material of the support can be adjusted to the different requirements in this area, as are placed on the film tube for example. Whereas the film tube should be substantially tear-resistant and durable, the passage region of the sound waves should offer good permeability for the sound waves and good adaptability to the transducer. That is why it is now possible in an embodiment in accordance with the invention to choose respective materials for the support which not only ensure reliable adhesion of the first adhesive, but also favorable properties with respect to sound passage. In accordance with a preferred embodiment, the support is provided with a thinner configuration than the film tube and is made of an elastomeric material. Elastomeric materials are able to deform elastically under tensile and pressure loads. As a result of the elasticity of an elastomeric material, the support will flexibly adjust to the respective transducer. The lower layer thickness of the support promotes sound passage.

It is further possible that the support has a curved initial shape. The curved initial shape can be adjusted especially to the curvature of the ultrasonic transducer. The support is therefore provided with a three-dimensional shaping in this case. If the support is additionally arranged elastically, this initial shape is deformable, but the support will always return to said three-dimensional initial shape. Such an embodiment ensures close contact with the ultrasonic transducer and prevents the formation of folds entirely.

The invention will be explained below by reference to embodiments shown in the enclosed drawings, wherein.

Figure 1:
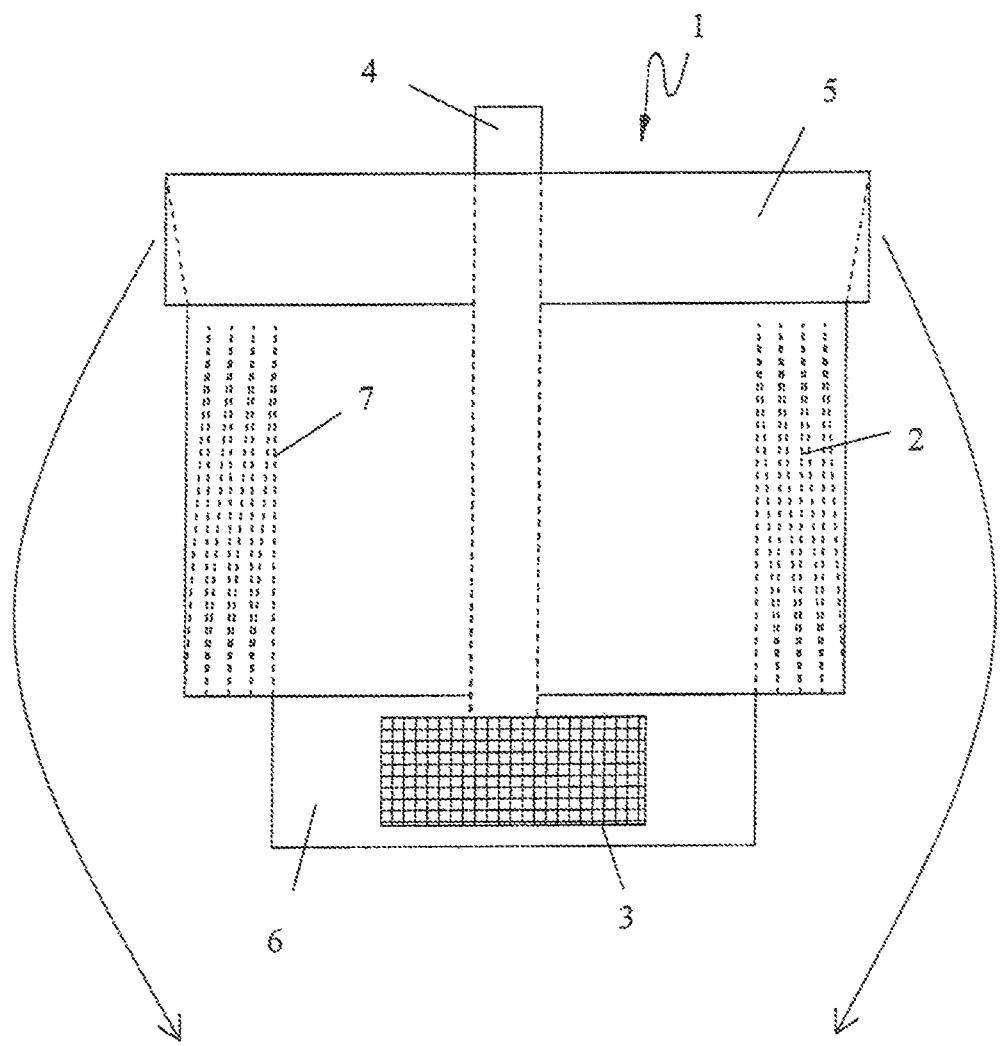
FIG. 1 shows a schematic illustration of a film tube in accordance with the invention in the stored state.

Before the actual invention will be discussed, an embodiment of a film tube will be explained at first which in the illustrated example is to be provided with a sterile configuration. The bag-like film tube in accordance with the invention comprises a shortening fold 2 in the stored state, which fold forms a pocket-like engagement area 1. The pocket-like engagement area 1 is formed by the innermost pocket-like folding layer 7 of the fold 2. Said innermost pocket-like folding layer 7 of the fold 2 comprises a closed end region 6 which protrudes beyond the outer folding layers. The exterior of the closed end region 6 therefore forms an outside surface section of the fold 2. An adhesive surface 3 is arranged on said outside surface section, which adhesive surface can be bordered by a visible marking for the purpose of better recognizability. The adhesive surface 3 is preferably formed by a sterilization-proof first adhesive.

Different variants are possible for producing the illustrated fold 2. One possibility is shown in FIG. 1, i.e. a fold 2 with folding layers which extend parallel to the longitudinal axis of the film tube.

At the opposite end, the fold 2 can converge into a cuff 5 which is not part of the fold 2. The outside surface of the cuff 5 forms an exterior section of the enclosure even in the in-use state of the film tube, but in regions remote from the patient however. Contamination of the cuff 5 by a non-sterile helper can therefore be tolerated.

As is further shown in FIG. 1, a guide strip 4 is fixed to the innermost pocket-like folding layer 7, which guide strip leads up to the exterior of the pocket-like engagement region 1. The guide strip 4 helps the treating person to find the correct engagement opening into the innermost pocket-like folding layer 7 and the detachment of any bonding of the innermost pocket-like folding layer 7. Preferably, the guide strip 4 is fixed to the interior of the closed end section 6 and is arranged as an adhesive strip with removable protective film.

The adhesive surface 3 on the outer surface section of the fold 2 corresponds in its extension substantially to the outlet surface of the sound waves in the ultrasonic transducer (not shown in FIG. 1). It preferably clearly protrudes beyond the outlet surface in order to enable better fixing to the ultrasonic transducer 8 on the one hand and to enable use for different configurations of ultrasonic devices on the other hand.

Before the arrangement of the adhesive surface 3 in accordance with the invention will be discussed below, the sterile application of a film tube in accordance with the invention will be explained below first. In the course of applying the film tube in accordance with the invention, an unsterile helper can remove the sterile packaged film tube from the packaging and touch the folded film tube on its outside. This outside then becomes unsterile. The helper then presents the folded film tube to the treating person, such that the helper tightly holds the folded film tube on the cuff 5.

The treating person then slips the sterile hand into the sterile pocket-like engagement region 1, which can be found easily with the help of the guide strip 4. The fingertips of this hand are then located in the region of the closed end section 6 of the innermost pocket-like folding layer 7.

The unsterile helper subsequently passes the ultrasonic transducer 8 (not shown in FIG. 1) which is approximately shaped like a mushroom to the treating person, with the sound surface being disposed in the upper region and the cable leads on its shaft. The treating person presses with his or her fingertips the exterior adhesive surface 3 against the ultrasonic transducer 8, with the outlet surface for the ultrasonic waves being fixed to the adhesive surface 3. The unsterile helper can now pull the folded film tube in the direction of the arrow shown in FIG. 1, i.e. in the direction of the ultrasonic transducer and its cable leads. If the film tube is arranged in the manner as shown in FIG. 1, the outside surface of the fold 2 forms inside sections of the enclosure for the ultrasonic device and its cable leads in the in-use state. The sterile inside surfaces of the fold 2 on the other hand form completely sterile outside surface sections of the enclosure.

The sterile hand of the treating person will be released again in the course of this turning-out process of the film tube and further grips the shaft of the ultrasonic transducer 8. If the guide strip 4 is arranged as an adhesive strip, it can be used to additionally seal the shaft of the ultrasonic device covered by the film tube slightly beneath the ultrasonic transducer 8. The film tube cover is then positioned securely and tightly on the ultrasonic device.

Figure 2:
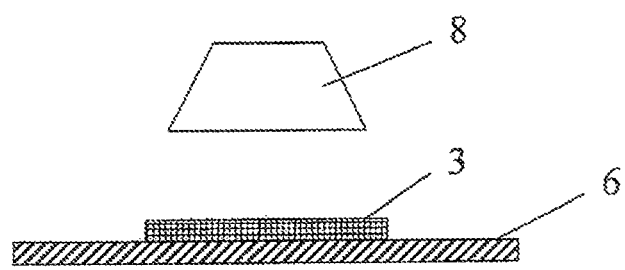
FIG. 2 shows a schematic illustration of an arrangement of an adhesive surface on a film tube in accordance with the state of the art.
Figure 3:
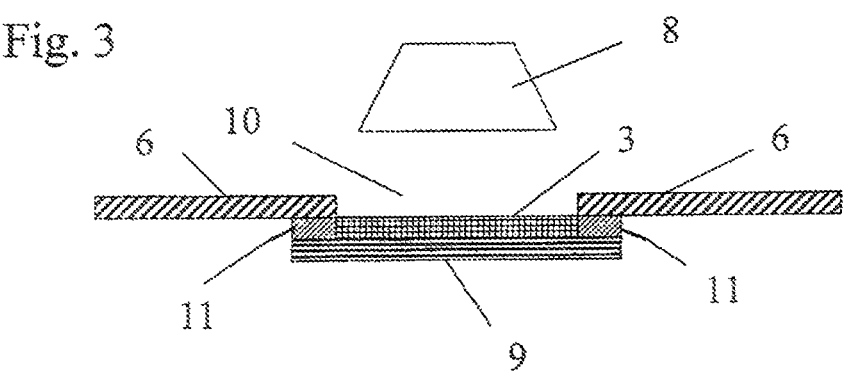
FIG. 3 shows a schematic illustration of a first embodiment of an arrangement of an adhesive surface on a film tube in accordance with the invention.
Figure 4:
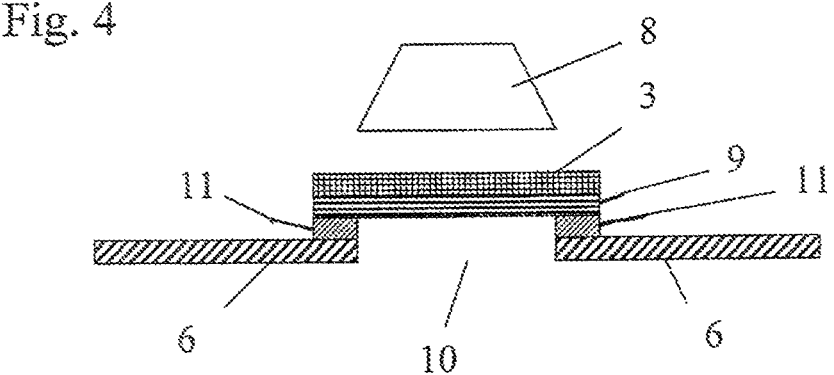
FIG. 4 shows a schematic illustration of a preferred embodiment of an arrangement of an adhesive surface on a film tube in accordance with the invention.

Reference is made below to FIGS. 2 to 4, with FIG. 2 showing a schematic illustration of an arrangement of an adhesive surface 3 on a film tube according to the state of the art. In this case, the adhesive surface 3 is applied directly to the end region 6 of the film tube. In such an embodiment, a part of the adhesive of the adhesive surface 3 will always remain as a residue on the ultrasonic transducer 8 after detachment, necessitating a careful and occasionally laborious cleaning of the ultrasonic transducer 8.

That is why it is proposed in accordance with the invention to provide a respectively arranged support 9 for the adhesive surface 3, wherein the first adhesive which is used for the adhesive surface 3 can be detached in a residue-free manner from the ultrasonic transducer 8 and remains completely on the support 9. Possible embodiments are shown in this respect in FIGS. 3 and 4, with the layer thicknesses of the film tube and the support as well as the adhesive layers being shown with excessive thickness in comparison with the ultrasonic transducer 8 for the purpose of better clarity of the illustration. The adhesive surface 3 will be provided in practice with a protective film (not shown in FIGS. 3 and 4), which protective film will be removed from the adhesive surface 3 prior to using the film tube for the purpose of exposing the adhesive surface 3.

FIG. 3 shows a schematic view of a first embodiment of an arrangement of an adhesive surface 3 in accordance with the invention on a film tube, with a sound opening 10 being provided in the end region 6 of the film tube, which sound opening is covered by the support 9. The support 9 is tightly connected with the film tube (preferably in a manner impermeable to germs), e.g. with the help of a second adhesive 11 which encloses the sound opening 10. The support 9 can also be made of a plastic material and be welded together with the film tube. The adhesive surface 3 is provided in the region of the sound opening 10, which adhesive surface faces the ultrasonic transducer 8.

A simple embodiment which therefore can be produced in a cost-effective way is shown in FIG. 4. In this case, the adhesive surface 3 is applied all over to the side of the support 9 which faces the ultrasonic transducer 8. The second adhesive 11 is applied in an annular manner on the side of the support which faces away from the ultrasonic transducer 8 and represents a tight connection (preferably impermeable to germs) with the end region 6 of the film tube. Alternatively, the support 9 can also be welded together with the film tube.

The sound opening 10 is therefore covered by the support 9 again, which in this manner becomes part of the germ-impermeable biological barrier of the film tube. The first adhesive of the adhesive surface 3 can have a lower adhesive force in comparison with the second adhesive 11 in order to be detached easily from the ultrasonic transducer 8. The second adhesive 11 can be provided with a high adhesive force in order to ensure a secure and preferably germ-impermeable connection of the support 9 with the film tube.

Since the film tube in accordance with the invention is to be frequently provided as a set with other medical instruments such as covers, needles, catheters etc, the exceptionally easy sterilization capability of the embodiment in accordance with the invention offers considerable advantages. A frequent type of sterilization occurs by means of ethylene oxide within the scope of so-called ETO sterilization, to which the film tube in accordance with the invention can easily be subjected. Preferably, a material is used for the first adhesive of the adhesive surface 3 and for the second adhesive 11 which is insensitive to ethylene oxide, so that the adhesive properties are not changed as a result of the sterilization process.

Respective materials are preferably chosen for the support 9 which not only ensure reliable bonding of the first adhesive, but also offer favorable properties concerning the passage of sound. As a result, the support 9 can be made in form of a support film made of plastic and be provided with a thinner configuration than the film tube, and can especially be made of an elastomeric material. Furthermore, homogeneous application of the adhesive surface 3 must be considered in order to ensure favorable adhesion of the ultrasonic transducer 8 on the support 9 by avoiding air pockets. It is advantageous in this respect if the support 9 has a curved initial state, with the curved initial state being adjusted to the curvature of the ultrasonic transducer 8. The support 9 is provided in this case with an elastic, three-dimensional shape.

The invention therefore provides a film tube which protects the ultrasonic transducer 8 and especially its sound surface in the best possible way, and avoids the use of a gel between the ultrasonic transducer 8 and the film tube. Repeated attachment and removal of the adhesive surface 3 has no negative effect on the sound surface because the adhesive surface 3 can be detached from the ultrasonic transducer 8 without any residues.

The invention claimed is:
1. A film tube cover for an ultrasonic transducer having a body with a sound passage region and cable leads which is arranged in the manner of a bag for enclosing a hand-operated ultrasonic transducer and the cable leads thereof, comprising:
    (a) an adhesive surface formed by a first adhesive for attaching the film tube cover to an ultrasonic transducer,
    (b) a support in form of a support film for the adhesive surface and adapted for positioning at least substantially across a passage region of the sound waves from ultrasonic transducer, and
    (c) wherein the film tube cover further comprises:
        (i) a sound opening in form of a recess having an area adapted for positioning at least substantially across a passage region of the sound waves of an ultrasonic transducer,
        (ii) the support film comprising a resiliently deformable, ultrasound permeable material and having a transducer side, an opposite side, and an area covering the sound opening and being tightly connected with the film tube cover bag around the sound opening, and
        (iii) the adhesive surface being applied all over to the area of the transducer side of the support at the sound opening and adapted to be pressed on and directly affixed at least substantially across a sound passage region of an ultrasonic transducer, the first adhesive having an adhesive force between the adhesive surface and the a sound passage region of an ultrasound transducer which is lower than between the adhesive surface and the support and lower than that tight connection between the support and the film tube cover bag;
    (d) so that the film tube cover protects the ultrasound transducer, and the adhesive surface and support can directly removably of the film tube cover at least substantially across a sound passage region of the ultrasound transducer without gel between them, deterring any folds or air gaps between them, promoting ultrasound permeability through them, and promoting residue-free detachment from the sound passage region of the ultrasound transducer over one or more attachments and removals.

2. A film tube cover according to claim 1, wherein the support is made of plastic and is welded together with the film tube cover.

3. A film tube cover according to claim 1, wherein the support is tightly connected with the film tube cover by means of a second adhesive.

4. A film tube cover according to claim 3, wherein the first adhesive of the adhesive surface and the second adhesive are arranged on opposite sides of the support.

5. A film tube cover according to claim 1, wherein the support is arranged to be thinner than the tube film cover bag.

6. A film tube cover according to claim 1, wherein the support is made of an elastomeric material.

7. A film tube cover according to claim 1, wherein the support has a curved initial state.

* * * * *

UNITED STATES PATENT AND TRADEMARK OFFICE
CERTIFICATE OF CORRECTION

| | | |
|---|---|---|
| PATENT NO. | : 9,131,921 B2 | |
| APPLICATION NO. | : 13/988290 | |
| DATED | : September 15, 2015 | |
| INVENTOR(S) | : Leopold Lackner | |

It is certified that error appears in the above-identified patent and that said Letters Patent is hereby corrected as shown below:

In the Claims

In column 6, Claim 1(b), line 38:

INSERT --an-- after the word from

In column 6, Claim 1(c)(iii), line 56:

DELETE "a" which occurs before the word sound

In column 6, Claim 1(d), line 63:

DELETE "of" which occurs after removably and
INSERT --affix-- after removably

Signed and Sealed this
Fifth Day of July, 2016

Michelle K. Lee
*Director of the United States Patent and Trademark Office*